United States Patent
Saka et al.

[11] Patent Number: 5,985,372
[45] Date of Patent: Nov. 16, 1999

[54] METHOD FOR PREPARING ANTIBACTERIAL/ANTIFUNGAL INORGANIC MATTER-COMPOSITED WOOD

[75] Inventors: Shiro Saka, Ohtsu; Fumie Tanno, Kyoto; Akira Yamamoto, Gunma-ken; Masaki Tanaka, Tokyo; Koichi Higuchi, Gunma-ken, all of Japan

[73] Assignee: Shin-Etsu Chemical Co., Ltd., Tokyo, Japan

[21] Appl. No.: 09/090,338

[22] Filed: Jun. 4, 1998

[30] Foreign Application Priority Data

Jun. 4, 1997 [JP] Japan ..................................... 9-160668
Jun. 20, 1997 [JP] Japan ..................................... 9-180468

[51] Int. Cl.$^6$ ....................................................... B05D 3/02
[52] U.S. Cl. ........................ 427/387; 427/297; 427/397; 427/440
[58] Field of Search .................................. 427/440, 297, 427/387, 397

[56] References Cited

U.S. PATENT DOCUMENTS 4,304,820  12/1981  Deubzer et al. ......................... 427/440
5,120,581   6/1992  Brunken et al. ........................ 427/440

FOREIGN PATENT DOCUMENTS 8-318509  12/1996  Japan .

*Primary Examiner*—Katherine A. Bareford
*Attorney, Agent, or Firm*—Miller, White, Zelano, & Branigan, P.C.

[57] ABSTRACT

An antibacterial/antifungal inorganic matter is composited with wood by impregnating wood with a solution containing a silicon alkoxide and an antibacterial/antifungal organic silicon compound having a hydrolyzable alkoxysilyl group, and subjecting the silicon compounds within the cell walls (inter- and intracellular) spaces to hydrolysis at various temperatures and polycondensation. The same is prepared by treating wood with a siloxane oligomer and curing the oligomer. The antibacterial/antifungal component is prevented from being leached out.

4 Claims, 2 Drawing Sheets

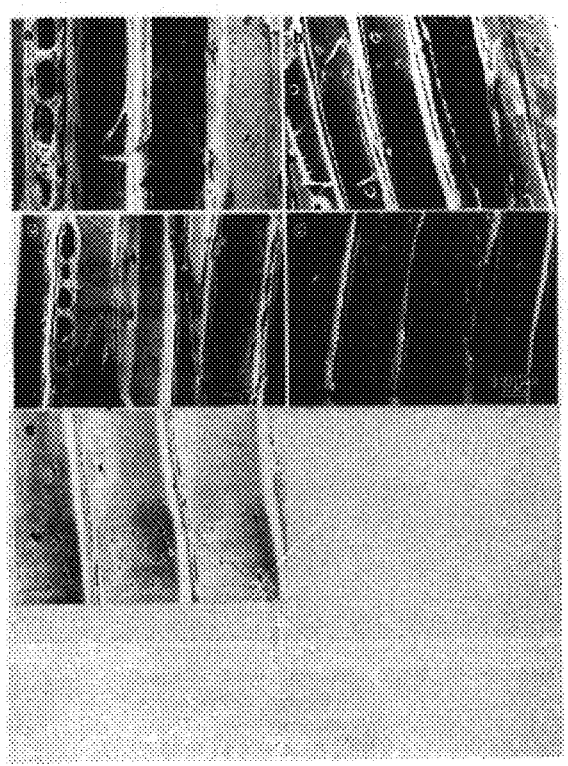

METHOD FOR PREPARING ANTIBACTERIAL/ANTIFUNGAL INORGANIC MATTER-COMPOSITED WOOD

BACKGROUND OF THE INVENTION

1. Field of the Invention

This invention relates to a method for preparing an antibacterial/antifungal inorganic matter-composited wood and more particularly, to a method for preparing an antibacterial/antifungal inorganic matter-composited wood having an antibacterial/antifungal component incorporated therein in such a manner that the antibacterial/antifungal component is prevented from being leached out in water and the antibacterial/antifungal function is semi-permanently imparted to wood.

2. Prior Art

The utilization of wood is often restricted by its characteristic features of "flammability," "biodeterioration" and "dimensional instability".

A number of proposals have been made for improving these properties. To impart antibacterial/antifungal and preservative functions, a variety of treatments have been proposed and practiced in the art.

One of the currently available preservative (antibacterial/antifungal) treatments is the application of creosote oil which has long been employed. The creosote oil is a mixture of aromatic hydrocarbons as a main component and numerous compounds. The creosote oil-treated wood found application as railroad ties and utility poles. As a wood preservative, the creosote oil has the advantages of low cost, ease of penetration and effective preservative action and the disadvantages of giving off stenchful and eye and skin-irritant fumes. When dissolved out, the creosote oil can contaminate the surrounding soil and leach into rivers or lakes where it is toxic to fish. In many aspects, the creosote oil imposes a heavy burden to the environment.

The exterior wood which is most frequently used at present is CCA-impregnated wood. The CCA is a water-soluble chemical agent containing copper (Cu), chromium (Cr) and arsenic (As) as basic chemicals. It is in wide-spread use over the world because the wood treated therewith exhibits excellent performance. However, the inclusion of such elements as chromium and arsenic draws concerns about the safety of this chemical agent. In some countries, the use of CCA is restricted. Since CCA-treated wood pieces are often used as play instruments in parks and schools, the influence of CCA on human bodies through skin contact is also a concern. With respect to oral toxicity, the toxicity of CCA must be carefully examined because CCA-treated wood pieces are used as outdoor play instruments for children. While acid rain now becomes one of the causes of global environmental damage, it is expected that CCA chemicals can be leached out of the wood with acid rain. When CCA-treated wood is burned for disposal, arsenides are sublimated from the CCA agent as diarsenic trioxide and released into the air, and oxides of copper and chromium are released as microparticulates. From the safety standpoint, the Environmental Protection Agency of USA rules that CCA-treated wood must not be burned in the open air or fireplaces. In UK, it is required that if one makes a fire in the open air using CCA-treated wood, the distance from houses must be at least 100 meters.

Since creosote oil and CCA impose heavy burdens on the environment as mentioned above, careful consideration must be made on their use at the present day when global environmental problems are highlighted. It is DDAC (didecyldimethylammonium chloride) that enjoys a rapidly growing share as a preservative agent for impregnation. This agent contains a metal salt. An increasing demand for DDAC is expected since DDAC avoids the problem associated with the disposal of wood which is of most concern in the case of CCA. Regrettably, the effect of DDAC does not last long and its semi-permanent fixation has not been realized. Besides, metal salts of naphthenic acid are used as a preservative of the surface treatment type and also as a chemical agent for pressure impregnation. They are known to be fully safe, but the retention of their effect is yet a problem. For this reason, the metal naphthenates are mainly used for the treatment of foundations (see "Wood Science Series 5—Environment," Kaisei-sha, 1995). The social demand for antibacterial/antifungal and bactericidal properties is very high as demonstrated in Japan during the prevalence of group food poisoning by pathogenic colibacillus O-157 in 1996. It is urgently required to develop a wood treating agent capable of retaining its effect semi-permanently and remaining safe.

Making investigations to develop high functional wood which is improved in environmental pollution and leach, we found a method for modifying wood by impregnating wood with a silicon alkoxide and subjecting it to hydrolysis and polycondensation to form silicon oxide fixedly within the wood cell walls (inter- and intracellular spaces) whereby various functions such as anti-rotting, dimensional stability and flame retardance are imparted to the wood as reported in the Journal of the Japan Wood Research Society, 38, 11, 1043 (1992). This method relies on the sol-gel process of metal alkoxide in that the starting solution of metal alkoxide-water-alcohol-catalyst converts into a sol of metal oxide through hydrolysis and self-polycondensation of the metal alkoxide. With further progress of reaction, the solution converts into a gel. When this reaction is carried out within wood cells, the inorganic matter based on metal oxide is incorporated into wood.

However, the recent research works revealed that the process of compositing wood with metal oxide largely depends on the rate of hydrolysis of a particular metal alkoxide used and that the distribution of metal oxide in wood cells largely varies with processing conditions. In the event of compositing wood with inorganic matter using a silicon alkoxide having a low rate of hydrolysis and subsequent polycondensation, for example, if the wood used is a moisture-conditioned piece of wood (water in wood is all bound water and present solely in cell walls), the hydrolysis and polycondensation reaction of the silicon alkoxide does proceed solely within the cell walls where bound water is present, resulting in inorganic matter-composited wood in which cell cavities are empty. This composited wood maintains the advantages of wood including light weight, strength and heat insulation, that is, it is modified wood which is provided with rot resistance, dimensional stability and flame retardance while maintaining the porous feature of wood (see the Journal of the Japan Wood Research Society, 39, 3, 301 (1993)). If the wood used is a water-saturated piece (not only cell walls but also cell cavities are full of water), there results in inorganic matter-composited wood in which not only cell walls but also cell cavities are filled with silicon dioxide (see the Journal of the Japan Wood Research Society, 39, 3, 301 (1993)).

If the metal alkoxide used is changed, there is obtained inorganic matter-composited wood having a completely different distribution. If a titanium alkoxide having a high rate of hydrolysis and subsequent polycondensation is used, for example, titanium oxide forms solely in cell cavities in the case of a moisture-conditioned piece. In the case of a water-saturated piece, oxide forms solely on the outer surface of the piece, but no metal oxide is composited in the interior of the piece. See the Journal of the Japan Wood Research Society, 39, 3, 308 (1993).

Based on these findings, we further investigated the relationship between the intracellular distribution of metal oxide and the function imparted thereby, and found that selective compositing of metal oxide in cell walls is a key for a minor amount of metal oxide formed to exert effective functions (see Wood Industry, 50, 9, 400 (1995)). Such compositing is possible with inorganic matter-composited wood based on silicon oxide resulting from silicon alkoxide. once distributed in wood cell walls, silicon oxide is not leached out in water or other solvents and semi-permanently fixed within cell walls.

SUMMARY OF THE INVENTION

Therefore, an object of the invention is to provide a method for preparing an inorganic matter-composited wood which is improved in environmental pollution and chemical leaching, is highly functional, and exerts an antibacterial/antifungal function over an extended term in a stable manner.

Based on the above-described results of our research and development works, we continued research works to develop inorganic matter-composited wood having an improved antibacterial/antifungal function. We have found that if silicon dioxide distributed and fixed in wood cell walls and an antibacterial/antifungal organic silicon compound form covalent bonds through Si—O—Si linkages, the antibacterial/antifungal component is semi-permanently fixed in the wood. The resulting inorganic matter-composited wood is capable of exerting a stable antibacterial/antifungal function over an extended term. More particularly, we have found a brand new technique capable of manufacturing an antibacterial/antifungal wood article in a simple and consistent manner without losing the original texture of wood itself. That is, when wood is impregnated with silicon alkoxide, use is made of a mixed solution containing not only a silicon alkoxide, but also an antibacterial/antifungal organic silicon compound having a hydrolyzable alkoxysilyl group and optionally, a water repellent organic silicon compound having a hydrolyzable alkoxysilyl group. Then these compounds are subjected to hydrolysis and polycondensation at various temperatures whereby the organic silicon compound forms a covalent bond with silicon dioxide and is thus fixed within the wood. The resulting inorganic matter-composited wood sustains the antibacterial/antifungal activity semi-permanently. When the water repellent function is imparted at the same time, the antibacterial/antifungal activity is further improved.

In a first aspect, the invention provides a method for preparing an antibacterial/antifungal inorganic matter-composited wood, comprising the steps of impregnating wood with a treating solution containing a silicon alkoxide and an antibacterial/antifungal organic silicon compound having a hydrolyzable alkoxysilyl group so that wood cell walls (inter- and intracellular spaces) are filled therewith, and subjecting the silicon alkoxide and the organic silicon compound within the inter- and intracellular spaces to hydrolysis and polycondensation at various temperatures.

The silicon alkoxide is of the following general formula (1):

$$(CH_3)_a Si(OR)_{4-a} \tag{1}$$

wherein R is a substituted or unsubstituted monovalent hydrocarbon group having 1 to 12 carbon atoms, and letter a is equal to 0, 1, 2 or 3.

Preferably, the organic silicon compound is of the following general formula (2):

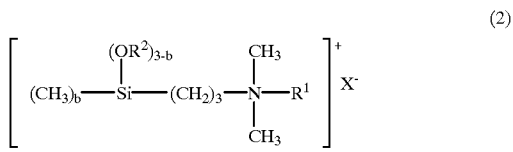

$$\left[ (CH_3)_b\!-\!\!\underset{\underset{\displaystyle }{|}}{\overset{\underset{\displaystyle (OR^2)_{3-b}}{|}}{Si}}\!-\!(CH_2)_3\!-\!\underset{\underset{\displaystyle CH_3}{|}}{\overset{\underset{\displaystyle CH_3}{|}}{N}}\!-\!R^1 \right]^{\!+}\! X^- \tag{2}$$

wherein $R^1$ is a monovalent aliphatic hydrocarbon group having 11 to 22 carbon atoms, $R^2$ is an alkyl group having 1 to 4 carbon atoms, X is a halogen atom, and letter b is equal to 0 or 1.

Preferably, the treating solution further contains another organic silicon compound of the following general formula (3):

$$R^3{}_m Si(OR^4)_{4-m} \tag{3}$$

wherein $R^3$ is a substituted or unsubstituted monovalent hydrocarbon group having 2 to 18 carbon atoms, $R^4$ is a monovalent hydrocarbon group having 1 to 6 carbon atoms, and letter m is equal to 1, 2 or 3. More preferably, at least one of the $R^3$ groups is a group wherein some or all of the hydrogen atoms attached to carbon atoms are replaced by fluorine atoms.

We have also found a brand new technique capable of manufacturing an antibacterial/antifungal wood article in a simple and consistent manner without losing the original texture of wood itself. By treating wood with a solution of a siloxane oligomer of the average compositional formula (4) shown later and heating the treated wood, alkoxides and silanols in the oligomer undergo hydrolysis and self-polycondensation whereby a sol of metal oxide is formed. Further progress of reaction converts the sol to a gel. Through this reaction, wood is composited with inorganic matter based on metal oxide. This method of preparing inorganic matter-composited wood can be practiced without paying attention to the safe working environment because of the low vapor pressure of the siloxane oligomer used. Since the leaching of silicon dioxide under the action of water is prevented, the composited wood exerts the antibacterial/antifungal activity over an extended term in a stable manner.

More particularly, by treating wood with a siloxane oligomer solution, subjecting the oligomer to hydrolysis at various temperatures and further to polycondensation for eventually curing the oligomer, a silicone resin containing an antibacterial/antifungal organic silicon compound and optionally, a water repellent organic silicon compound is incorporated in the wood. There is obtained an inorganic matter-composited wood article having antibacterial/antifungal activity. The water repellent function given by the water repellent organic silicon compound helps the antibacterial/antifungal organic silicon compound exert its function. In a further embodiment wherein an organic silicon compound having an amino group is additionally used, the solubility of the siloxane oligomer in a solvent is improved. Particularly when the solubility of the siloxane oligomer in water is improved, the siloxane oligomer can be used as an aqueous solution.

In a second aspect, the invention provides a method for preparing an antibacterial/antifungal inorganic matter-composited wood, comprising the steps of treating wood with a siloxane oligomer and curing the siloxane oligomer. The siloxane oligomer is of the following average compositional formula (4):

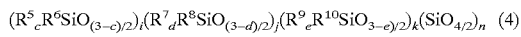

$$(R^5_c R^6 SiO_{(3-c)/2})_i (R^7_d R^8 SiO_{(3-d)/2})_j (R^9_e R^{10} SiO_{3-e)/2})_k (SiO_{4/2})_n \quad (4)$$

wherein $R^5$, $R^7$ and $R^9$ are hydrogen or halogen- or cyano-substituted or unsubstituted monovalent hydrocarbon groups having 1 to 10 carbon atoms, $R^6$ is a halogen- or cyano-substituted or unsubstituted monovalent hydrocarbon groups having 1 to 18 carbon atoms, $R^8$ is an amino-bearing monovalent organic group having 1 to 18 carbon atoms, $R^{10}$ is a monovalent organic group of the general formula (5):

$$[—(CH_2)_3NR^{11}(CH_3)_2]^+X^- \quad (5)$$

wherein $R^{11}$ is a monovalent hydrocarbon group of 11 to 22 carbon atoms and X is a halogen atom, letters c, d, and e are equal to 0 or 1, i, j and n are 0 or positive numbers, and k is a positive number with proviso that both i and n are not equal to 0. The siloxane oligomer is terminated with a hydroxyl group and/or an alkoxy group of 1 to 4 carbon atoms.

According to the invention, there is provided a safe and practical method for preparing inorganic matter-composited wood wherein the antibacterial/antifungal activity is improved due to the water repellence of the silicone resin. The term "antibacterial/antifungal activity" or function is used in a broader sense to encompass preservative and bactericidal activities as well.

BRIEF DESCRIPTION OF THE DRAWINGS

FIG. 2 is a photomicrograph of wood rotten with brown rot fungus, sections (a), (b), (c), (d) and (e) corresponding to the test pieces of Comparative Example 1, Comparative Example 2, Comparative Example 4, Example 2, and Example 5, respectively.

DETAILED DESCRIPTION OF THE INVENTION

Figures 1A, 1B:
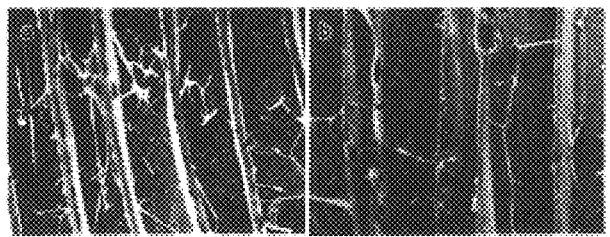
FIG. 1 is a photomicrograph of wood rotten with white rot fungus, sections (a), (b), (c), (d) and (e) corresponding to the test pieces of Comparative Example 1, Comparative Example 2, Comparative Example 4, Example 2, and Example 5, respectively.

The starting wood used herein is not critical. Logs, sawed lumber, sliced veneer, and plywood are included. The species of tree is not critical.

First Embodiment

The first method involves impregnating wood with a solution containing a silicon alkoxide and an antibacterial/antifungal organic silicon compound.

The silicon alkoxide used herein is of the general formula (1).

$$(CH_3)_a Si(OR)_{4-a} \quad (1)$$

R is selected from substituted or unsubstituted monovalent hydrocarbon groups having 1 to 12 carbon atoms, preferably 1 to 4 carbon atoms, for example, alkyl groups such as methyl, ethyl, propyl, isopropyl, butyl, hexyl, octyl, decyl and dodecyl. Preferably R is selected from alkyl groups of 1 to 4 carbon atoms such as methyl, ethyl, propyl, isopropyl and butyl. Letter a is equal to 0, 1, 2 or 3, preferably equal to 0 or 1.

The silicon alkoxides of formula (1) may be used alone or in admixture of two or more.

The antibacterial/antifungal organic silicon compound having a hydrolyzable alkoxysilyl group is preferably of the following general formula (2):

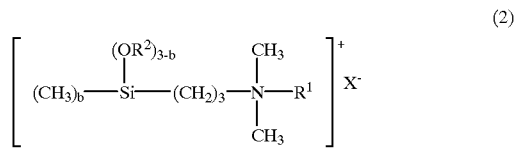

(2)

wherein $R^1$ is a monovalent aliphatic hydrocarbon group having 11 to 22 carbon atoms, $R^2$ is an alkyl group having 1 to 4 carbon atoms, X is a halogen atom, and letter b is equal to 0 or 1.

The monovalent aliphatic hydrocarbon groups of 11 to 22 carbon atoms represented by $R^1$ may be either saturated or unsaturated and either normal or branched hydrocarbon groups. Some or all of the hydrogen atoms attached to carbon atoms may be replaced by substituents such as hydroxyl groups and halogen atoms. Exemplary are octadecyl, lauryl, myristyl, and stearyl. Examples of the alkyl group represented by $R^2$ are methyl, ethyl, propyl and butyl. The halogen atoms represented by X include chlorine, bromine and iodine.

The compound of formula (2) is an organic silicon compound having a quaternary ammonium base and terminated with a hydrolyzable alkoxysilyl group and having an antibacterial/antifungal function. Because of the absence of toxic heavy metal atoms, this compound does not pollute the soil and rivers and has very low toxicity to humans. Additionally, it is less irritant and less odorous.

The organic silicon compound of formula (2) can be readily prepared as a quaternary ammonium salt type compound by reacting a compound having a 3-halogenopropyl group and an alkoxyl group each directly attached to a silicon atom, for example, 3-chloropropyltrimethoxysilane with an amine compound of the formula: $R^1N(CH_3)_2$ wherein $R^1$ is a monovalent aliphatic hydrocarbon group of 11 to 22 carbon atoms, for example, $C_{16}H_{33}N(CH_3)_2$ or $C_{18}H_{37}(CH_3)_2$ in a suitable solvent such as dimethylformamide at an elevated temperature.

An appropriate amount of the antibacterial/antifungal organic silicon compound added is 0.0001 to 0.5 mol, more preferably 0.001 to 0.01 mol per mol of the silicon alkoxide of formula (1). Greater amounts of the organic silicon compound outside this range would rather adversely affect the antibacterial/antifungal effect.

In one preferred embodiment of the invention, the treating solution further contains a water-repellent organic silicon compound having a hydrolyzable alkoxysilyl group. This organic compound is preferably of the following general formula (3):

$$R^3_m Si(OR^4)_{4-m} \quad (3)$$

$R^3$ is selected from substituted or unsubstituted monovalent hydrocarbon groups having 2 to 18 carbon atoms, preferably 2 to 12 carbon atoms, for example, alkyl groups such as ethyl, propyl, butyl, pentyl, and hexyl. Also included are substituted hydrocarbon groups in which some or all of the hydrogen atoms attached to carbon atoms are replaced by substituents such as halogen atoms and cyano groups, for example, perfluoroalkyl groups such as 3,3,3-trifluoropropyl, 2-(heptafluorobutyl)ethyl and 2-(heptadecafluorooctyl)ethyl, perfluoropolyether groups, and cyano-substituted groups such as cyanoethyl. Preferred among others are halogen-substituted alkyl groups in which some or all of the hydrogen atoms attached to carbon atoms are replaced by halogen atoms, especially fluorine-containing groups such as perfluoroalkyl and perfluoroether groups. $R^4$ is selected from monovalent hydrocarbon groups having 1 to 6 carbon atoms, especially 1 to 4 carbon atoms, typically alkyl groups of 1 to 6 carbon atoms and alkenyl groups of 2 to 6 carbon atoms, for example, such as methyl, ethyl, propyl, butyl, pentyl, hexyl, ethynyl and propenyl. Letter m is equal to 1, 2 or 3 and preferably equal to 1.

Examples of the compound of formula (3) include 3,3,3-trifluoropropyltrimethoxysilane, 2-(heptafluorobutyl)ethyltrimethoxysilane, 2-(heptadecafluorooctyl)ethyltrimethoxysilane, and 3,3,3-trifluoropropyltriethoxysilane.

An appropriate amount of the organic silicon compound of formula (3) added is 0.0001 to 0.5 mol, most preferably about 0.01 mol per mol of the silicon alkoxide of formula (1). Greater amounts outside this range would rather fail to provide uniform water repellence.

The first method for preparing an antibacterial/antifungal inorganic matter-composited wood is carried out as follows. To a solution containing one or more silicon alkoxides of formula (1) are added an antibacterial/antifungal organic silicon compound having a hydrolyzable alkoxysilyl group of formula (2) and optionally, a water-repellent organic silicon compound having a hydrolyzable alkoxysilyl group of formula (3). A moisture-conditioned piece of wood is impregnated with the treating solution so that wood inter- and intracellular spaces are filled with the solution. The silicon alkoxide and the organic silicon compound(s) within the inter- and intracellular spaces are subjected to hydrolysis, followed by polycondensation, thereby forming silicon oxide with which the antibacterial/antifungal organic silicon compound forms a covalent bond and the optional water-repellent organic silicon compound also forms a covalent bond. The treated wood piece is finally dried.

The treating solution may also be obtained by using a mixed solution of the silicon alkoxide and the organic silicon compound or using dilutions of the respective compounds in suitable solvents such as alcohols, acetone, aliphatic hydrocarbons or aromatic hydrocarbons. Acidic or alkaline catalysts may be added or not.

In impregnating wood with the mixed solution, the wood may be in a moisture-conditioned or water-saturated state, preferably in a state conditioned to a water content of 10 to 50% by weight. The wood may be directly immersed in the mixed solution. A vacuum or pressure impregnation technique may also be used.

The wood is kept immersed in the mixed solution at room temperature under a vacuum of about 10 to 15 mmHg for about 1 to about 7 days. Thereafter, the wood is taken out of the solution, allowed to stand at room temperature for about one day, and heated for drying at about 50 to 110° C. for about ½ to about 2 days. In this process, the silicon alkoxide is hydrolyzed at various temperatures and then polycondensed whereby it is converted into silicon dioxide which is fixed within cell walls. At the same time, the organic silicon compound(s) coexisting with the silicon alkoxide form covalent bonds with the silicon dioxide whereby they are semi-permanently fixed within the wood.

Second Embodiment

The second method for preparing an antibacterial/antifungal inorganic matter-composited wood involves the steps of treating wood with a siloxane oligomer and curing the siloxane oligomer.

The siloxane oligomer is of the following average compositional formula (4):

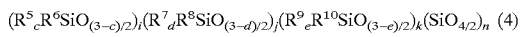

wherein $R^5$, $R^7$ and $R^9$ are hydrogen or halogen- or cyano-substituted or unsubstituted monovalent hydrocarbon groups having 1 to 10 carbon atoms, $R^6$ is a halogen- or cyano-substituted or unsubstituted monovalent hydrocarbon groups having 1 to 18 carbon atoms, $R^8$ is an amino-bearing monovalent organic group having 1 to 18 carbon atoms, $R^{10}$ is a monovalent organic group of the general formula (5):

wherein $R^{11}$ is a monovalent hydrocarbon group of 11 to 22 carbon atoms and X is a halogen atom, letters c, d, and e are equal to 0 or 1, preferably 0, i, j and n are 0 or positive numbers, and k is a positive number with proviso that both i and n are not equal to 0. The siloxane oligomer is terminated with a hydroxyl group and/or an alkoxy group of 1 to 4 carbon atoms.

The monovalent hydrocarbon groups represented by $R^5$, $R^7$ and $R^9$ include alkyl groups such as methyl, ethyl, propyl, butyl, pentyl, hexyl, octyl, and decyl; alkenyl groups such as vinyl, allyl, propenyl and butenyl; aryl groups such as phenyl and tolyl; aralkyl groups such as benzyl and phenylethyl; substituted hydrocarbon groups in which some or all of the hydrogen atoms attached to carbon atoms are replaced by substituents such as halogen atoms and cyano groups, for example, fluorine-substituted alkyl groups such as 3,3,3-trifluoropropyl, 2-(heptafluorobutyl)ethyl and 2-(heptadecafluorooctyl)ethyl, fluorine-substituted polyether groups, and cyano-substituted groups such as cyanoethyl.

Examples of the substituted or unsubstituted hydrocarbon groups represented by $R^6$ include the same examples as described for $R^5$, $R^7$ and $R^9$ as well as long-chain alkyl groups such as lauryl, myristyl and stearyl, and substituted ones thereof in which some or all of the hydrogen atoms are replaced by halogen atoms such as fluorine. Preferably, $R^6$ is selected from halogen-substituted alkyl groups in which some or all of the hydrogen atoms are replaced by halogen atoms, especially fluorine-substituted alkyl groups.

$R^8$ is preferably an amino-bearing monovalent organic group of the formula:

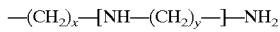

wherein x is 1 to 8, especially 1 to 6, y is 2 to 10, especially 2 to 6, and z is 0 to 8, especially 0 to 5.

$R^{10}$ is a monovalent organic group of the general formula (5):

wherein $R^{11}$ is preferably a long chain alkyl or alkenyl group.

Each of the units $R^5_c R^6 SiO_{(3-c)/2}$, $R^7_d R^8 SiO_{(3-d)/2}$, and $R^9_e R^{10} SiO_{(3-e)/2}$ may be a mixture of different structures.

In particular, the $R^5_c R^6 SiO_{(3-c)/2}$ unit, which is to impart water repellence to wood, is preferably composed of $CH_3SiO_{3/2}$ units and $R'SiO_{3/2}$ units wherein $R'$ is alkyl of 5 to 18 carbon atoms or $CH_3SiO_{3/2}$ units and $R''SiO_{3/2}$ units wherein $R''$ is fluorinated alkyl of 1 to 18 carbon atoms. Herein, the content of $CH_3SiO_{3/2}$ units is preferably 5 to 100 mol % of the $R^5_c R^6 SiO_{(3-c)/2}$ unit.

The letters i, j, k and n are as defined above. Provided that i+j+k+n=1, i is preferably from 0 to 0.9999 and especially from 0.1 to 0.9 (that is, 0≦i≦0.9999, especially 0.1≦i≦0.9). Letter j is preferably 0 to 0.800 (that is, 0≦j≦0.800). It is noted that the $R^7_d R^8 SiO_{(3-d)/2}$ unit with suffix j is introduced when it is desired to impart water solubility to the siloxane oligomer. Letter k is a positive number and preferably from 0.0001 to 0.5 and especially from 0.001 to 0.2 (that is, 0.0001≦k≦0.5, and especially 0.001≦k≦0.2). Letter n is preferably 0 to 0.9999 (that is, 0≦n≦0.9999). Both i and n are not equal to 0. That is, when i is 0, n is a positive number. When n is 0, i is a positive number.

The siloxane oligomer of formula (4) preferably has an average degree of polymerization of 2 to 20. If the degree of polymerization is more than 20, a longer time is required for impregnation.

The siloxane oligomer of formula (4) can be obtained by a conventional process of effecting co-hydrolysis of an antibacterial/antifungal organic silicon compound and a water-repellent organic silicon compound and/or a tetrafunctional silicon alkoxide such as tetramethoxysilane or tetraethoxysilane and optionally, an amino-bearing organic silicon compound. Alternatively, the silicon alkoxide and the organic silicon compound(s) are independently previously subjected to partial hydrolysis before they are mixed and co-hydrolyzed.

The tetrafunctional silicon alkoxide used herein is usually of the following general formula (6):

$$Si(OR^{12})_4 \qquad (6)$$

wherein $R^{12}$ is an alkyl group of 1 to 4 carbon atoms.

The antibacterial/antifungal organic silicon compound used herein is usually of the following general formula (7):

$$R^9_e R^{10} Si(OR^{13})_{3-e} \qquad (7)$$

wherein $R^9$, $R^{10}$ and e are as defined above, and $R^{13}$ is an alkyl group of 1 to 4 carbon atoms.

The compound of formula (7) is an organic silicon compound having a quaternary ammonium base and terminated with a hydrolyzable alkoxysilyl group and having an antibacterial/antifungal function. Because of the absence of toxic heavy metal atoms, this compound does not pollute the soil and rivers and has very low toxicity to humans. Additionally, it is less irritant and less odorous.

The organic silicon compound of formula (7) can be readily prepared as a quaternary ammonium salt type compound by reacting a compound having a 3-halogenopropyl group and an alkoxyl group each directly attached to a silicon atom, for example, 3-chloropropyltrimethoxysilane with an amine compound of the formula: $R^{11}N(CH_3)_2$ wherein $R^{11}$ is a monovalent hydrocarbon group of 11 to 22 carbon atoms, for example, $C_{16}H_{33}N(CH_3)_2$ or $C_{18}H_{37}(CH_3)_2$ in a suitable solvent such as dimethylformamide at an elevated temperature.

The water-repellent organic silicon compound may be of the following general formula (8):

$$R^5_c R^6 Si(OR^{14})_{3-c} \qquad (8)$$

wherein $R^5$, $R^6$ and c are as defined above, and $R^{14}$ is an alkyl group of 1 to 4 carbon atoms. Examples of the compound of formula (8) include methyltrimethoxysilane, methyltriethoxysilane, 3,3,3-trifluoropropyltrimethoxysilane, 2-(heptafluorobutyl) ethyltrimethoxysilane, 2-(heptadecafluorooctyl) ethyltrimethoxysilane, 3,3,3-trifluoropropyltriethoxysilane, 3,3,3-trifluoropropylmethyldimethoxysilane, and 3,3,3-trifluoropropylmethyldiethoxysilane.

The amino-bearing organic silicon compound may be of the following general formula (9):

$$R^7_d R^8 Si(OR^{15})_{3-d} \qquad (9)$$

wherein $R^7$, $R^8$, and d are as defined above, and $R^{15}$ is an alkyl group of 1 to 4 carbon atoms. Examples of the compound of formula (9) include 3-aminopropyltrimethoxysilane, 3-aminopropyltriethoxysilane, N-(2-aminoethyl)-3-aminopropyltrimethoxysilane, N-(2-aminoethyl)-3-aminopropyltriethoxysilane, and N-(2-aminoethyl)-3-aminopropylmethyldimethoxysilane.

The alkoxysilanes of the above formulae (6) to (9) are reacted in such amounts that i, j, k and n may satisfy the above-mentioned molar fractions.

In the hydrolysis step, catalysts such as acidic catalysts, alkaline catalysts, fluoride catalysts, and transition metal compound catalysts may be used.

When wood is treated with the siloxane oligomer of formula (4), the siloxane oligomer may be used as such or after diluting with suitable organic solvents, for example, alcohols such as methyl alcohol and ethyl alcohol and ketones such as acetone and methyl ethyl ketone. However, the use of organic solvents is not recommended because strict restriction is now made on organic solvents and the use of organic solvents can lead to environmental damage. The siloxane oligomer of formula (4) according to the invention is soluble in water when j>0 in formula (4), that is, when a siloxane unit having an amino-bearing monovalent organic group is contained. Then the siloxane oligomer can be diluted with water which is the preferred diluent.

To the siloxane oligomer described above, an additional organic silicon compound such as dimethyldimethoxysilane or methyldimethoxysilane may be added and mixed for imparting flexibility to the resin. In this embodiment, when the siloxane oligomer is prepared, the additional organic silicon compound may be added to tetraethoxysilane or a partial hydrolyzate thereof whereupon it is subject to co-hydrolysis. Further, to impart termite-resistant properties, a termite-resistant ingredient such as boric acid may be added. The termite-resistant ingredient may be added during the reaction to form the siloxane oligomer or post-added to the oligomer.

For the treatment of wood with the siloxane oligomer solution, the wood is preferably in a moisture-conditioned state although the state of wood is not critical. The treatment may be done by impregnation, spraying, brush coating, dipping, and vacuum or pressure impregnation.

After treatment with the siloxane oligomer, the wood is dried at an elevated temperature in the range which does not cause pyrolysis of wood, for example, 50 to 110° C. During the process, the solvent volatilizes off and the oligomer is concentrated, hydrolyzed, then polycondensed and cured whereby the oligomer converts into a silicone resin having antibacterial/antifungal activity.

It is noted that the above-described siloxane oligomer finds another application because of its antibacterial/antifungal activity. For example, fibrous cellulose paper such as wall paper can be similarly treated with the siloxane oligomer to impart antibacterial/antifungal activity thereto.

The method for preparing an antibacterial/antifungal inorganic matter-composited wood according to the invention has the advantage that since the antibacterial/antifungal and water-repellent organic silicon compounds are used along with the silicon alkoxide, the antibacterial/antifungal component is semi-permanently fixed within the wood and water repellence is also imparted for further improving the antibacterial/antifungal activity. Then wood is given an anti-rotting (antibacterial/antifungal) function while preventing the extraction or leaching of the antibacterial/antifungal component which has never been prevented in the prior art, and without obstructing the bonding and coating functions of wood during working. By carrying out the method of the invention, there can be produced on a large scale a large volume of antibacterial/antifungal wood which is suitable as members in open areas complying with the Japanese building standards, interior members and exterior members.

EXAMPLE

Examples of the invention are given below by way of illustration and not by way of limitation.

Physical properties of inorganic matter-composited wood were examined by the following tests.

(1) Weight Percent Gain

A test piece of wood was subjected to Soxhlet extraction with acetone and water each for 24 hours before the absolute dry weight (Wu) of the untreated wood piece was determined. Then the test piece was treated for inorganic matter compositing and dried at 105° C. for 24 hours. The absolute dry weight (Wt) of the inorganic matter-composited wood piece was determined. A weight percent gain (WG) of the inorganic matter-composited wood was calculated according to $$WG(\%)=(Wt-Wu)/Wu \times 100$$

(2) Wood Rotting test Using White and Brown Rot Fungi

For examining antibacterial/antifungal activity, a rotting test was made on inorganic matter-composited wood according to the Japan Wood Preservation Association (JWPA) Standard, No. 3 (1992), Durability Test Method for Wooden Material. After test pieces were dried and sterilized at 6020 C. for 48 hours, they were placed on lawns of white rot fungus Coriolus versicolor (L. ex Fr.) Quel (IFO 30340) and brown rot fungus Tyromyces palustris (Berk. et Curk. Murr.) (IFO 30390) which had been fully grown in culture dishes in a glass container. After cultivation in an incubator at room temperature (26° C.) and a relative humidity of 55 to 65% for 8 weeks, the test pieces were taken out, and the fungal cells were wiped off from the surface. The absolute dry weight of the test pieces was determined. A percent weight loss by wood-rot fungus was calculated from the absolute dry weight of the test pieces before the test.

(3) SEM Examination of Wood-rot Fungi

Using a microtome, a thin section was cut from the interior of the test piece obtained in the rotting test (2). After gold evaporation, the section was observed under a scanning electron microscope for observing the growth of wood-rot fungi.

(4) Subterranean Rotting Test

Test pieces of untreated wood and inorganic matter-composited wood were subjected to Soxhlet extraction with acetone and water each for 24 hours. A subterranean test of burying the test pieces in non-sterilized soil 17 cm deep from the ground surface was carried out for 9 months. A percent weight loss was calculated from the absolute dry weights of each test piece before and after the burying test, from which the progress of decay was presumed.

EXAMPLE 1

Veneer pieces of cypress sapwood (50 mm×100 mm×1 mm thick) were subjected to Soxhlet extraction with acetone and water each for 24 hours, and conditioned to a moisture content of 25%. To a reaction solution composed of tetra-ethoxysilane (TEOS, $Si(OC_2H_5)_4$), ethanol, and acetic acid in a molar ratio of 1:1:0.01, a 40 wt % methanol solution of 3-(trimethoxysilyl)propyloctadecyldimethylammonium chloride (TMSAC) was added so as to give a molar ratio of 0.001 mol of TMSAC per mol of TEOS. The wood pieces were impregnated with this reaction solution at room temperature under vacuum for 3 days. Thereafter, the wood pieces were heated at 65° C. for 24 hours and then at 105° C. for 24 hours for ripening the resulting gel, obtaining pieces of inorganic matter-composited wood. These pieces had a weight gain (WG) of 4.6% mainly by silicon dioxide. After the 8-week wood rotting test using white and brown rot fungi, they showed weight losses of 3.0% and 4.0%, respectively. After the 9-month subterranean rotting test, they showed a weight loss of 10.4%.

EXAMPLE 2

Pieces of inorganic matter-composited wood were obtained as in Example 1 except that the amount of TMSAC added was changed to a molar ratio of 0.005 mol of TMSAC per mol of TEOS. These pieces had a weight gain (WG) of 5.6%. After the rotting test using white and brown rot fungi, they showed weight losses of 2.4% and 2.8%, respectively. After the subterranean test, they showed a weight loss of 5.4%. The results are shown in Table 1.

EXAMPLE 3

Pieces of inorganic matter-composited wood were obtained as in Example 1 except that the amount of TMSAC added was changed to a molar ratio of 0.01 mol of TMSAC per mol of TEOS. These pieces had a weight gain (WG) of 8.1%. After the rotting test using white and brown rot fungi, they showed weight losses of 2.9% and 0.4%, respectively. After the subterranean test, they showed a weight loss of 7.8%. The results are shown in Table 1.

EXAMPLE 4

Pieces of inorganic matter-composited wood were obtained as in Example 1 except that 2-(heptadecafluorooctyl)ethyltrimethoxysilane (HFOETMOS) was further added to the reaction solution in a molar ratio of 0.004 mol per mol of TEOS. These pieces had a weight gain (WG) of 4.8%. After the rotting test using white and brown rot fungi, they showed a weight loss of 0% for both. After the subterranean test, they showed a weight loss of 1.7%. The results are shown in Table 1.

EXAMPLE 5

Pieces of inorganic matter-composited wood were obtained as in Example 2 except that 2-(heptadecafluorooctyl)ethyltrimethoxysilane (HFOETMOS) was further added to the reaction solution in a molar ratio of 0.004 mol per mol of TEOS. These pieces had a weight gain (WG) of 7.0%. After the rotting test using white and brown rot fungi, they showed a weight loss of 0% for both. After the subterranean test, they showed a weight loss of 3.1%. The results are shown in Table 1.

EXAMPLE 6

Pieces of inorganic matter-composited wood were obtained as in Example 3 except that 2-(heptadecafluorooctyl)ethyltrimethoxysilane (HFOETMOS) was further added to the reaction solution in a molar ratio of 0.004 mol per mol of TEOS. These pieces had a weight gain (WG) of 8.8%. After the rotting test using white and brown rot fungi, they showed a weight loss of 0% for both. After the subterranean test, they showed a weight loss of 2.7%. The results are shown in Table 1.

Comparative Example 1

Using the same procedure and conditions as in Examples 1 to 6, pieces of untreated wood were subjected to the rotting test using white and brown rot fungi whereupon they showed weight losses of 10.7% and 7.9%, respectively. After the subterranean test, they showed a weight loss of 21.6%. The results are shown in Table 1.

Comparative Example 2

Pieces of inorganic matter-composited wood were obtained as in Example 1 except that TMSAC was not added to the reaction solution. These pieces had a weight gain Comparative Example 5

Pieces of TMSAC-treated wood were obtained as in Example 1 except that in the reaction solution, TEOS was omitted and the same volume of ethanol was added instead, and the amount of TMSAC (40 wt % methanol solution) added was increased so as to give a molar ratio of 0.01. These pieces had a weight gain (WG) of 1.8%. After the rotting test using white and brown rot fungi, they showed weight losses of 1.7% and 2.2%, respectively, indicating relatively good results. After the subterranean test, however, they showed a fairly increased weight loss of 9.0%. The results are shown in Table 1.

TABLE 1

| | Silicon compound | | | Weight loss (%) | | |
| | Metal alkoxide | Antibacterial/ antifungal one | Water repellent one | Weight gain (%) | White rot fungus | Brown rot fungus | 9-month subterranean test |
|---|---|---|---|---|---|---|---|
| E1 | TEOS | TMSAC | — | 4.6 | 3.0 | 4.0 | 10.4 |
| E2 | TEOS | TMSAC | — | 5.6 | 2.4 | 2.8 | 5.4 |
| E3 | TEOS | TMSAC | — | 8.1 | 2.9 | 0.4 | 7.8 |
| E4 | TEOS | TMSAC | HFOETMOS | 4.8 | 0 | 0 | 1.7 |
| E5 | TEOS | TMSAC | HFOETMOS | 7.0 | 0 | 0 | 3.1 |
| E6 | TEOS | TMSAC | HFOETMOS | 8.8 | 0 | 0 | 2.7 |
| CE1 | — | — | — | 0 | 10.7 | 7.9 | 21.6 |
| CE2 | TEOS | — | — | 6.5 | 11.4 | 4.3 | 18.0 |
| CE3 | — | TMSAC | — | 0.1 | 5.1 | 5.3 | 15.6 |
| CE4 | — | TMSAC | — | 1.0 | 5.5 | 5.8 | 6.9 |
| CE5 | — | TMSAC | — | 1.8 | 1.7 | 2.2 | 9.0 |

TEOS: tetraethoxysilane
TMSAC: 3-(trimethoxysilyl)propyloctadecyldimethylammonium chloride
HFOETMOS: 2-(heptadecafluorooctyl)ethyltrimethoxysilane (WG) of 6.5%. After the rotting test using white and brown rot fungi, they showed weight losses of 11.4% and 4.3%, respectively. After the subterranean test, they showed a weight loss of 18.0%. The results are shown in Table 1.

Comparative Example 3

Pieces of TMSAC-treated wood were obtained as in Example 1 except that in the reaction solution, TEOS was omitted and the same volume of ethanol was added instead. These pieces had a weight gain (WG) of 0.1%. After the rotting test using white and brown rot fungi, they showed weight losses of 5.1% and 5.3%, respectively, indicating relatively good results. After the subterranean test, they showed a weight loss of 15.6%, indicating low antibacterial/ antifungal activity against the 9-month test. The results are shown in Table 1.

Comparative Example 4

Pieces of TMSAC-treated wood were obtained as in Example 1 except that in the reaction solution, TEOS was omitted and the same volume of ethanol was added instead, and the amount of TMSAC (40 wt % methanol solution) added was increased so as to give a molar ratio of 0.005. These pieces had a weight gain (WG) of 1.0%. After the rotting test using white and brown rot fungi, they showed weight losses of 5.5% and 5.8%, respectively. After the subterranean test, they showed a weight loss of 6.8%. The results are shown in Table 1.

Figures 1C, 1D:
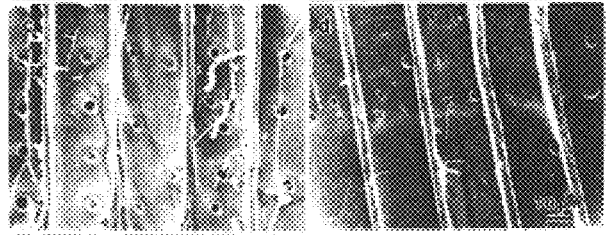
Figure 1E:

FIG. 1 is a collection of SEM photomicrographs of the test pieces rotten with white rot fungus of Examples 2 and 5 and Comparative Example 1, 2 and 4. FIG. 2 is a collection of similar SEM photomicrographs of the test pieces rotten with brown rot fungus. In FIGS. 1 and 2, sections (a), (b), (c), (d), and (e) correspond to the test pieces of Comparative Example 1, Comparative Example 2, Comparative Example 4, Example 2, and Example 5, respectively. Many white and brown rot fungi are observed in (a), (b), and (c), but few in (d) and (e).

EXAMPLE 7

A 1-liter flask was charged with 208 grams (1.0 mol) of tetraethoxysilane (TEOS), 2.8 grams (0.005 mol) of 2-(heptadecafluorooctyl)ethyltrimethoxysilane (HFOETMOS), 2.5 grams (0.005 mol) of 3-(trimethoxysilyl)propyloctadecyldimethylammonium chloride (TMSAC), 0.5 gram (0.008 mol) of acetic acid, and 208 grams of methanol. With stirring at room temperature, 36 grams of deionized water was added dropwise to the flask for reaction to take place, and the reaction solution was ripened at 50° C. for 1 hour. Then, 0.9 grams (0.005 mol) of 3-aminopropyltrimethoxysilane (APTMOS) was added dropwise to the flask for reaction to take place, and the reaction solution was ripened at 50° C. for 1 hour. The solution was diluted with methanol to a solution containing 10% by weight of the resulting oligomer, which was used for treatment. This oligomer had the average composition:

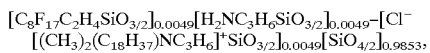

and an average degree of polymerization of about 6, and was terminated with methoxy and hydroxyl groups.

Veneer pieces of cypress sapwood (50 mm×100 mm×1 mm thick) were subjected to Soxhlet extraction with acetone and water each for 24 hours, and conditioned to a moisture content of 25%. The wood pieces were impregnated with the oligomer solution at room temperature under vacuum for 3 days. Thereafter, the wood pieces were heated at 65° C. for 24 hours and then at 105° C. for 24 hours for ripening the resulting gel, obtaining pieces of inorganic matter-composited wood. These pieces had a weight gain (WG) of 11.0% mainly by silicon dioxide. After the 8-week wood rotting test using white and brown rot fungi, they showed a weight loss of 0% for both. After the 9-month subterranean rotting test, they showed a weight loss of 2.5%.

EXAMPLE 8

Reaction was carried out as in Example 7 except that 5 grams (0.01 mol) of TMSAC was used and APTMOS was omitted. The reaction solution was diluted with methanol to a solution containing 10% by weight of the oligomer, which was used for treatment. This oligomer had the average composition:

$$[C_8F_{17}C_2H_4SiO_{3/2}]_{0.0049}[Cl^-[(CH_3)_2(C_{18}H_{37})NC_3H_6]^+SiO_{3/2}]_{0.0099}[SiO_{4/2}]_{0.9852}$$

and an average degree of polymerization of about 8, and was terminated with methoxy and hydroxyl groups.

Using this oligomer solution, pieces of inorganic matter-composited wood were obtained as in Example 7. These pieces had a weight gain (WG) of 10.5%. After the rotting test using white and brown rot fungi, they showed a weight loss of 0% for both. After the subterranean test, they showed a weight loss of 2.8%.

Comparative Example 6

Using the same procedure and conditions as in Example 7, pieces of untreated wood were subjected to the rotting test using white and brown rot fungi whereupon they showed weight losses of 11.0% and 8.9%, respectively. After the subterranean test, they showed a weight loss of 22.8%.

Comparative Example 7

Reaction was carried out as in Example 7 except that TMSAC was omitted. The reaction solution was diluted with methanol to a solution containing 10% by weight of the oligomer, which was used for treatment. This oligomer had the average composition:

$$[C_8F_{17}C_2H_4SiO_{3/2}]_{0.0050}[H_2NC_3H_6SiO_{3/2}]_{0.0050}[SiO_{4/2}]_{0.9900}$$

and an average degree of polymerization of about 5, and was terminated with methoxy and hydroxyl groups.

Using this oligomer solution, pieces of inorganic matter-composited wood were obtained as in Example 7. These pieces had a weight gain (WG) of 9.3%. After the rotting test using white and brown rot fungi, they showed weight losses of 11.5% and 5.3%, respectively. After the subterranean test, they showed a weight loss of 18.9%.

EXAMPLE 9

Reaction was carried out as in Example 7 except that TEOS was omitted. The reaction solution was diluted with methanol to a solution containing 10% by weight of the oligomer, which was used for treatment. This oligomer had the average composition:

$$[C_8F_{17}C_2H_4SiO_{3/2}]_{0.3333}[H_2NC_3H_6SiO_{03/2}]_{0.3333}-[Cl^-[(CH_3)_2(C_{18}H_{37})NC_3H_6]^+SiO_{3/2}]_{0.3333}$$

and an average degree of polymerization of about 4, and was terminated with methoxy and hydroxyl groups.

Using this oligomer solution, pieces of inorganic matter-composited wood were obtained as in Example 7. These pieces had a weight gain (WG) of 0.5%. After the rotting test using white and brown rot fungi, they showed weight losses of 5.5% and 4.7%, respectively. After the subterranean test, they showed a weight loss of 14.9%.

Example 10

Reaction was carried out as in Example 7 except that HFOETMOS was omitted. The reaction solution was diluted with methanol to a solution containing 10% by weight of the oligomer, which was used for treatment. This oligomer had the average composition:

$$[H_2NC_3H_6SiO_{3/2}]_{0.0050}[Cl^-[(CH_3)_2(C_{18}H_{37})NC_3H_6]^+SiO_{3/2}]_{0.0050}[SiO_{4/2}]_{0.9900}$$

and an average degree of polymerization of about 4, and was terminated with methoxy and hydroxyl groups.

Using this oligomer solution, pieces of inorganic matter-composited wood were obtained as in Example 7. These pieces had a weight gain (WG) of 8.7%. After the rotting test using white and brown rot fungi, they showed weight losses of 1.5% and 2.5%, respectively. After the subterranean test, they showed a weight loss of 7.9%.

EXAMPLE 11

A 1-liter flask was charged with 136 grams (1.0 mol) of methyltrimethoxysilane (MTMOS), 2.6 grams (0.01 mol) of decyltrimethoxysilane (DTMOS), 5 grams (0.01 mol) of 3-(trimethoxysilyl)propyloctadecyldimethylammonium chloride (TMSAC), 90 grams (1.5 moles) of acetic acid, and 500 grams of t-butanol. With stirring at room temperature, 27 grams (1.5 moles) of deionized water was added dropwise to the flask for reaction to take place, and the reaction solution was ripened at 50° C. for 1 hour. Then, 179 grams (1.0 mol) of 3-aminopropyltrimethoxysilane (APTMOS) was added dropwise to the flask for reaction to take place, and the reaction solution was ripened at 50° C. for 1 hour. The solution was diluted with t-butanol to a solution containing 10% by weight of the resulting oligomer, which was used for treatment. This oligomer had the average composition:

$$[C_{10}H_{21}SiO_{3/2}]_{0.005}[H_2NC_3H_6SiO_{3/2}]_{0.4950}-[Cl^-[(CH_3)_2(C_{18}H_{37})NC_3H_6]^+SiO_{3/2}]_{0.005}[CH_3SiO_{3/2}]_{0.4950}$$

and an average degree of polymerization of about 5, and was terminated with methoxy, hydroxyl and t-butoxy groups.

Using this oligomer solution, pieces of inorganic matter-composited wood were obtained as in Example 7. These pieces had a weight gain (WG) of 9.5%. After the rotting test using white and brown rot fungi, they showed a weight loss of 0% for both. After the subterranean test, they showed a weight loss of 2.8%.

EXAMPLE 12

The procedure of Example 11 was repeated except that instead of t-butanol, deionized water was added to the reaction solution for dilution, obtaining an aqueous solution of 5% oligomer. Using this oligomer solution, pieces of inorganic matter-composited wood were obtained as in Example 7. These pieces had a weight gain (WG) of 7.6%. After the rotting test using white and brown rot fungi, they showed a weight loss of 0% for both. After the subterranean test, they showed a weight loss of 3.6%.

Although some preferred embodiments have been described, many modifications and variations may be made thereto in light of the above teachings. It is therefore to be understood that the invention may be practiced otherwise than as specifically described without departing from the scope of the appended claims.

We claim:

1. A method for preparing an antibacterial/antifungal inorganic matter-composited wood, comprising the steps of:

impregnating wood with an impregnating solution containing a silicon alkoxide and an antibacterial/antifungal organic silicon compound having a hydrolyzable alkoxysilyl group so that wood cell walls, inter- and intracellular spaces, are filled therewith, the silicon alkoxide being of the following general formula (1):

   $$(CH_3)_a Si(OR)_{4-a} \quad (1)$$

wherein R is a substituted or unsubstituted monovalent hydrocarbon group having 1 to 12 carbon atoms, and letter a is equal to 0, 1, 2 or 3, and the antibacterial/antifungal organic silicon compound being of the following general formula (2):

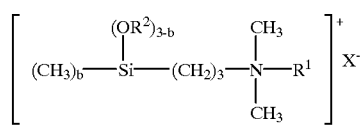

$$\left[ (CH_3)_b\!\!-\!\!\underset{(OR^2)_{3-b}}{Si}\!\!-\!\!(CH_2)_3\!\!-\!\!\underset{CH_3}{\overset{CH_3}{N}}\!\!-\!\!R^1 \right]^+ X^- \quad (2)$$

wherein $R^1$ is a monovalent aliphatic hydrocarbon group having 11 to 22 carbon atoms, $R^2$ is an alkyl group having 1 to 4 carbon atoms, X is a halogen atom, and letter b is equal to 0 or 1, and subjecting the silicon alkoxide and the organic silicon compound within the cell walls, the inter- and intracellular spaces, to hydrolysis at various temperatures and polycondensation.

2. The method of claim 1 wherein said impregnating solution further contains an organic silicon compound of the following general formula (3):

   $$R^3{}_m Si(OR^4)_{4-m} \quad (3)$$

wherein $R^3$ is a substituted or unsubstituted monovalent hydrocarbon group having 2 to 18 carbon atoms, $R^4$ is a monovalent hydrocarbon group having 1 to 6 carbon atoms, and letter m is equal to 1, 2 or 3.

3. The method of claim 2 wherein in formula (3), at least one of the $R^3$ groups is a group wherein some or all of the hydrogen atoms attached to carbon atoms are replaced by fluorine atoms.

4. A method for preparing an antibacterial/antifungal inorganic matter-composited wood, comprising the steps of impregnating wood with a siloxane oligomer and curing the siloxane oligomer, said siloxane oligomer being of the following average compositional formula (4):

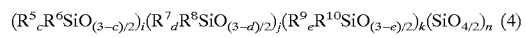
   $$(R^5{}_c R^6 SiO_{(3-c)/2})_i (R^7{}_d R^8 SiO_{(3-d)/2})_j (R^9{}_e R^{10} SiO_{(3-e)/2})_k (SiO_{4/2})_n \quad (4)$$

wherein $R^5$, $R^7$ and $R^9$ are hydrogen or halogen- or cyano-substituted or unsubstituted monovalent hydrocarbon groups having 1 to 10 carbon atoms, $R^6$ is a halogen- or cyano-substituted or unsubstituted monovalent hydrocarbon groups having 1 to 18 carbon atoms, $R^8$ is an amino-bearing monovalent organic group having 1 to 18 carbon atoms, $R^{10}$ is a monovalent organic group of the general formula (5):

   $$[-\!(CH_2)_3 NR^{11}(CH_3)_2]^+ X^- \quad (5)$$

wherein $R^{11}$ is a monovalent hydrocarbon group of 11 to 22 carbon atoms and X is a halogen atom, letters c, d, and e are equal to 0 or 1, i, j and n are 0 or positive numbers, and k is a positive number with proviso that both i and n are not equal to 0, said siloxane oligomer being terminated with a hydroxyl group and/or an alkoxy group of 1 to 4 carbon atoms.

* * * * *